United States Patent [19]

Machat

[11] Patent Number: 5,630,810
[45] Date of Patent: May 20, 1997

[54] METHOD OF OPHTHALMOLOGICAL SURGERY

[76] Inventor: Jeffery J. Machat, 12 Kettredge Court, Richmond Hill, Ontario, Canada, L4C 7X3

[21] Appl. No.: 606,504

[22] Filed: Feb. 23, 1996

Related U.S. Application Data

[63] Continuation of Ser. No. 238,857, May 6, 1994, abandoned.

[51] Int. Cl.$^6$ .................................................. A61N 5/06
[52] U.S. Cl. ............................... 606/5; 606/3; 606/10; 128/898
[58] Field of Search .................... 606/2, 3–6, 10–13; 128/897, 898

[56] References Cited

U.S. PATENT DOCUMENTS

| | | | |
|---|---|---|---|
| 4,665,913 | 5/1987 | L'Esperance, Jr. | 128/303.1 |
| 4,669,466 | 6/1987 | L'Esperance, Jr. | 128/303.1 |
| 4,718,418 | 1/1988 | L'Esperance, Jr. | 128/303.1 |
| 4,721,379 | 1/1988 | L'Esperance, Jr. | 351/212 |
| 4,729,372 | 3/1988 | L'Esperance, Jr. | 128/303.1 |
| 4,732,148 | 3/1988 | L'Esperance, Jr. | 128/303.1 |
| 4,770,172 | 9/1988 | L'Esperance, Jr. | 128/303.1 |
| 4,773,414 | 9/1988 | L'Esperance, Jr. | 128/303.1 |
| 4,798,204 | 1/1989 | L'Esperance, Jr. | 128/303.1 |
| 4,856,513 | 8/1989 | Muller | 128/303.1 |
| 4,903,695 | 2/1990 | Warner et al. | 606/4 |
| 4,941,093 | 7/1990 | Marshall et al. | 364/413.01 |
| 4,994,058 | 2/1991 | Raven et al. | 606/5 |
| 5,019,074 | 5/1991 | Muller | 606/5 |
| 5,108,388 | 4/1992 | Trokel | 606/5 |

FOREIGN PATENT DOCUMENTS

| | | | |
|---|---|---|---|
| 1243732 | 10/1988 | Canada | 327/1.2 |

OTHER PUBLICATIONS

Elements of Ultraviolet Laser Ablation, Srinivasan, Date of Publication Unknown.

Photoablative reprofiling of the cornea using an excimer laser: Photorefractive keratectomy, Marshall et al., 1986.

Excimer Laser Surgery of the Cornea, Trokel et al., Dec. 1983.

Laser Corneal Surgery, Steinert et al., 1988.

Long–term Healing of the Central Cornea after Photorefractive Keratectomy Using an Excimer Laser, Marshall et al., Oct. 1988.

Central Photorefractive Keratectomy for Myopia, MacDonald et al., Jun. 1990.

Excimer Laser (193 nm) Myopic Keratomileusis in Sighted and Blind Human Eyes, Seiler et al., Jun. 1990.

Central Photorefractive Keratectomy for Myopia, MacDonald et al., Sep. 1991.

On the Safety of 193–Nanometer Excimer Laser Refractive Corneal Surgery, Van Meilaert et al., 1992.

Excimer Laser Photorefractive Keratectomy, Gartry et al., Aug. 1992.

Philosophy and Technique for Excimer Laser Phototherapeutic Keratectomy, Thompson et al., Mar. 1993.

Corneal topography following excimer photorefractive keratectomy for myopia, Lin et al., 1993.

Corneal topography: In Search of the Excimer Islands, Gilbert, Fall 1993.

Changes in Corneal Topography after Excimer Laser Photorefractive Keratectomy for Myopia, Wilson et al., Date of Publication Unknown.

*Primary Examiner*—David Shay
*Attorney, Agent, or Firm*—Kvas Miller Everitt

[57] ABSTRACT

An improved method of ophthalmological surgery is disclosed. The method is used to change the optical characteristics of an eye through subjecting the eye's cornea to ultraviolet irradiation thereby volumetrically removing corneal tissue by way of photoablative decomposition. The method comprises the further step of subjecting a central portion of the cornea to increased ultraviolet irradiation and photoablative decomposition, over and above the irradiation of other corneal tissue. The effect is an increase in qualitative visual results while not significantly changing the refractive characteristic of the cornea.

10 Claims, 2 Drawing Sheets

METHOD OF OPHTHALMOLOGICAL SURGERY

This is a continuation of application Ser. No. 08/238,857, filed May 6, 1994, now abandoned.

FIELD OF THE INVENTION

This invention relates to the field of ophthalmological surgery and specifically to a method of photorefractive keratectomy for improving the optical and refractive characteristics of an eye. In particular the invention relates to a method of preventing the formation of central islands during photorefractive keratectomy.

BACKGROUND OF THE INVENTION

The human eye functions much like a camera in that light passes through the frontal portion of the eye and is focussed to produce an image on the rear surface or retina. There arc two primary focusing elements to the eye; the cornea and the lens, with the cornea providing the majority of the focusing power. Like film at the back of a camera, in order for an image to be seen clearly by the eye it must be focused precisely on the retina. When the focal point of the eye is for some reason altered and the image is not sharply focused on the retina, eyeglasses or contact lenses are often used to correct the problem.

Under normal circumstances the human eye is somewhat spherical with a frontal bulge comprising the cornea and the lens. However, over 70 million people in North America alone suffer from nearsightedness or myopia wherein there is a mismatch between the length of the eye and the shape of the cornea, with the cornea being generally too steep for the length of the eye. Under these circumstances light is focused on a spot in front of the retina resulting in a blurred or out of focused image. Another somewhat common visual impairment, and one that often accompanies myopia, is corneal astigmatism. Corneal astigmatism occurs when the cornea is a football or toric shape with the two major meridians having radii of different lengths. In the case of corneal astigmatism, the eye focuses at two different positions either in front or behind the retina causing a distortion or tilting of images received. In the case of hyperopia, a third form of visual impairment, the focal point of the eye is located behind the retina resulting in images that are out of focus, unless there is adequate muscular accommodation.

Traditionally myopia, astigmatism and hyperopia have been treated or corrected through the use of glasses or contact lens which adjust the light received by the eye to focus images on the surface of the retina, As an alternative to the use of such corrective lenses, it has been known that surgically altering the shape of the cornea will achieve essentially the same result. That is, through selectively altering the profile or anterior radius of the cornea's curvature, the refractive characteristics of the eye can be changed and improved, resulting in sharper visual imaging upon the retina and hence clearer unaided sight.

There are a number of techniques that have been employed to effect such modifications to the cornea. These techniques include: keratomileusis, epikeratophakia, keratophakia, radial keratotomy, and the use of plastic inserts. Keratomileusis involves the removal of a portion of the cornea and reshaping it while frozen before replacing the corrected removed portion back onto the cornea. In epikeratophakia the epithelium is removed and a synthetic or donor lenticle is sutured in place. Keratophakia involves placing a donor cornea/button into a pocket created in the patient's corneal stroma.

Radial keratotomy is a significantly different procedure that involves the cutting of a number of deep radial incisions that extend from the optical zone to the periphery of the cornea. As a result of these incisions the peripheral cornea bulges outwardly causing central corneal flattening and a reduction of its reflective power that may correct myopia. Transverse keratotomics, or T-cuts as they are sometimes known, when made perpendicular to the astigmatic axis can correct astigmatism.

Although each of these 5 methods can be useful when treating visual impairment of the types discussed, each also suffers from inherent problems. For example, keratomileusis may produce glare problems and sometimes creates irregular astigmatism. In addition, all these methods of refractive surgery have significant inherent problems; being primarily problems of predictability, ease of performing the procedure and surgical complications. When dealing with the elective correction of the refractive characteristics of the eye, extremely fine tolerances must be observed when removing or incising tissue. Extremely small variations in tolerances can result in significant diopter changes in refraction. A further problem with corneal surgery is that it is important that the procedure not impair the transparency or degrade the optical quality of the cornea. Incisions made within the optical region of the cornea must be made with great care so as to preserve the anatomical relationships of the corneal epithelium and minimize the incidence of stromal scaring and hence loss in transparency. Furthermore, in radial keratotomy the tissue below the keratotomies sustain mild damage leading to endothelial cell loss. In effect whenever mechanical means are employed to incise tissue some resulting damage to surrounding tissue will result. This fact is consistent no matter how fine the blade on the cutting tool that is used or how experienced the surgeon.

In response to the shortcomings and problems with these refractive surgery techniques, excimer laser keratectomy has been developed. With the introduction of ultraviolet lasers it was found that tissue from the anterior surface of the cornea could be removed through photoablation. Photoablution is the process where ultraviolet photons are absorbed by tissue molecules placing the molecules in a state of excitation. The increased energy state of the molecules "loosens" the bonds between the atoms causing the bonds to break in tiny bursts which can be described as very tiny explosions. The tissue under these conditions is said to "ablate". Since the ablation process involves the breaking of molecular bonds without significant heating, tissue damage is limited to the area of exposure.

The laser found to be best suited for this application is an argon fluoride excimer laser operating at a wavelength of 193 nm. Using such a laser, corneal tissue can be removed with a high degree of precision and with virtually no damage to adjacent or underlying unexposed surfaces. Excimer laser machines have been developed that supply pulsed ultraviolet radiation calibrated to ablate corneal tissue to a precise known depth. Such a laser beam can be configured in any cross-sectional shape and is accurately controlled as it strikes the cornea through the use of computerization. This no-touch method allows a surgeon to remove corneal tissue precisely without fear of damaging surrounding tissue. Laser keratectomy can then be carried out without the problems associated with the use of mechanical cutting means such as in radial keratotomy.

There are two basic forms of excimer laser beam configuration used in laser keratectomy; broad beam and narrow scanning beam. Narrow scanning laser beams suffer from their own inherent limitations and problem, however they are outside the general scope of this invention which deals more specifically with broad or wide beam configurations. Broad beam excimer lasers allow a surgeon to produce wide areas of photoablation such that the anterior surface of the cornea can be directly reprofiled to alter its optical power. For example, in the case of myopia, a portion of the central part of the cornea can be photoablated causing the cornea to be flattened with a corresponding reduction in dioptic power. Similarly through altering the targeting on the cornea, more tissue can be removed from the periphery of the cornea causing a steepening of the cornea to treat hyperopia. This process of correcting refractive error is commonly referred to as photorefractive keratectomy or PRK.

Although photorefractive keratectomy has proven to be a significant advancement in the field of optical correction of visual myopia, astigmatism and other corneal surface irregularities the procedure has not been without its problems. Laser refractive surgeons have increasingly reported surface irregularities after photorefractive keratectomy which result in side effects from the surgery. Of particular significance are central islands or elevations that often appear in the otherwise smooth corneal surface following PRK. Central islands are generally defined as topographic areas of steepening of at least 3 diopters and 3 millimeters in diameter, measured at least one month post-operatively. Central islands are normally time related and significantly prolong visual rehabilitation. Most often central islands eventually disappear, however, some may continue to exist indefinitely. Although quantitatively the patient's vision may be improved, qualitatively there may be significant visual impairments. Patients with central islands following PRK typically complain of "ghosting", monocular diplopia, and glare and distortion problems.

The precise cause of central island formation has heretofore not been totally understood. In an attempt to explain the cause of these central islands some researchers have proposed what has been referred to as the vortex plume theory. This theory proposes that the plume that is formed above the cornea during the ablation process blocks portions of the laser beam leaving a zone with less irradiation treatment; hence forming the topographical anomaly known as a central island. Operating under this theory, some researchers have proposed blowing nitrogen across the cornea during ablative treatment to eliminate the formation of central islands. However, purging the surface debris plume has been found to result in an increase in anterior-stromal reticular haze, regression, irregular astigmatism with slow visual rehabilitation and loss of best corrected visual acuity. The effect of central islands normally dissipates over time and normally within a few months they have either regressed or their effects have become only minimal. In more severe cases where central islands persist, they are retreated with a second excimer laser ablation confined specifically to the island itself.

Another theory advanced by some to explain the formation of central islands is known as the optic degradation theory. The theory is based upon the premise that central islands are formed as a result of the degradation of the optical characteristics of excimer lasers over time. Research has shown that this theory appears unsupportable since the incidence of central islands does not seem to vary between new and old lasers. One would expect that under the theory new lasers would have a lower incidence of central island formation. In addition, under the optic degradation theory nitrogen purging and the use of alcohol to remove the epithelium should have no significant effect on central island formation. This has been found not to be the case.

From the perspective of treating a patient using photorefractive keratectomy, the incidence of central islands is of concern since they have a significant effect upon the duration of the patient's recovery, sometimes require further treatment, produce visual distortion and may be permanent.

SUMMARY OF THE INVENTION

The invention therefore provides a method for overcoming the problems associated with photorefractive keratectomy by providing a method of improving the refractive characteristics of the eye through photoablation while minimizing or eliminating central island formation.

Accordingly, the invention in one of its aspects provides an improved method of ophthalmological surgery to change the optical characteristics of an eye, through subjection to ultraviolet irradiation to volumetrically remove corneal tissue by way of photoablative decomposition, the method comprising the further step of subjecting a central portion of the cornea to increased ultraviolet irradiation and photoablative decomposition, over and above the irradiation of other corneal tissue, to increase qualitative visual results while not significantly changing the refractive characteristic of the cornea.

In yet a further embodiment, the present invention provides a method of photorefractive keratectomy for making myopic or astigmatic corrections to an eye and thereby improving the refractive characteristics of the eye, the method comprising the steps of: (i) determining the portion of the cornea to be treated thereby defining a treatment area; (ii) selectively treating the anterior surface of the cornea by subjecting the central portion of the corneal tissue and epithelium in the treatment area to ultraviolet irradiation through the use of an excimer laser having a wavelength of 193 nm, whereby a portion of the corneal tissue, together with the overlying epithelium, is volumetrically removed through photoablative decomposition; and, (iii) subjecting the entire corneal tissue and epithelium in the treatment area to ultraviolet irradiation through exposure to said excimer laser causing volumetric removal of the epithelium, and volumetric removal of a predetermined depth of the corneal tissue, by means of photoablative decomposition.

In still yet a further embodiment, the present invention provides a method for reducing the incidence of central island formation in the cornea of an eye through minimizing the effects of acoustic shock waves within the eye's cornea during photorefractive keratectomy, the method comprising the steps of: (i) determining the portion of the cornea to be treated thereby defining a treatment area; (ii) removing the epithelium from the treatment area; (iii) forming a central hollow or detent, having a diameter of approximately 1 to 4 millimeters, in the corneal tissue through treating the central portion of said corneal tissue with an excimer laser having a wavelength of 193 nm; and (iv) subjecting the entire treatment area to irradiation through exposure to said excimer laser causing removal of a predetermined depth of corneal tissue, whereby acoustic shock waves created during the irradiation of the entire treatment area drive stromal fluid into the central area of the cornea.

Further objects and advantages of the invention will become apparent from the following description of the preferred embodiment.

BRIEF DESCRIPTION OF THE DRAWINGS

For a better understanding of the present invention, and to show more clearly how it may be carried into effect, reference will now be made, by way of example, to the accompanying drawings which show the preferred embodiment of the present invention in which.

DESCRIPTION OF PREFERRED EMBODIMENT

Figure 1:
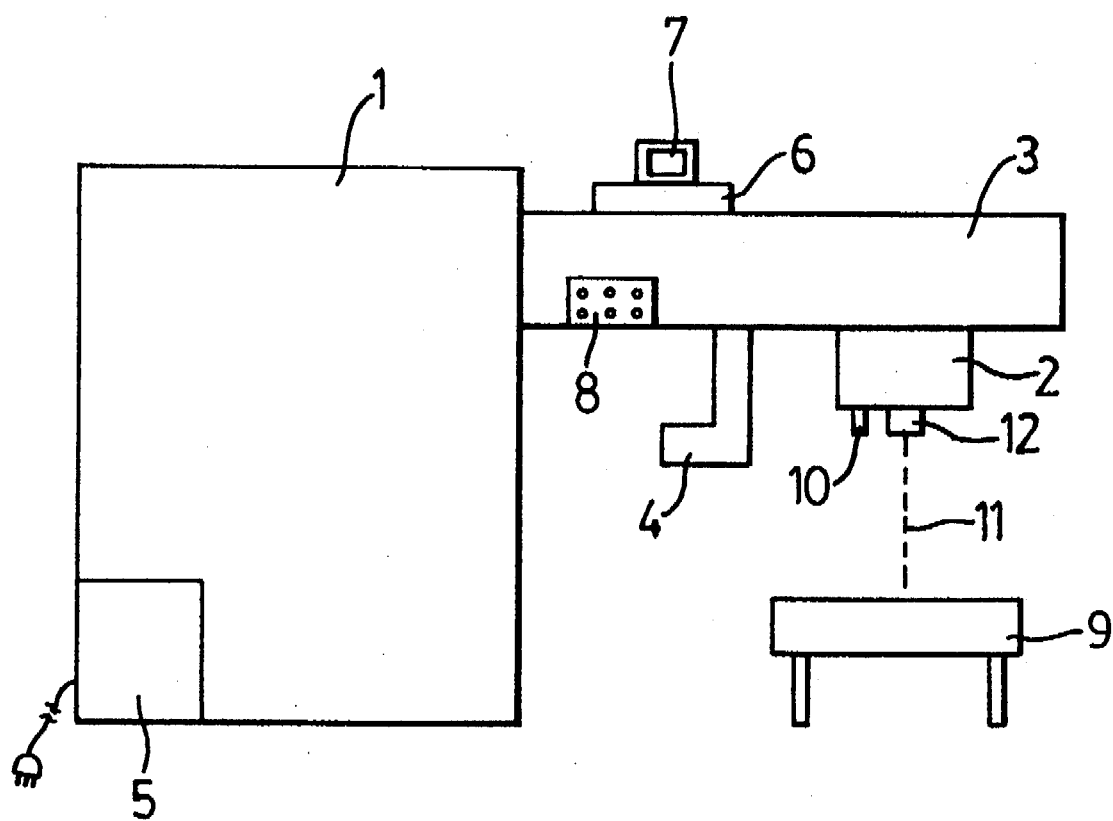
FIG. 1 is a schematic drawing showing the components of an excimer laser system pursuant to the invention.

In an attempt to explain the formation of corneal central islands, the inventor has determined that the vortex plume theory does not adequately explain the formation of such islands. Through further study it has been found that central islands are commonly formed through the use of excimer lasers having a flat beam profile (such as the VISX Twenty/Twenty Excimer Laser and the Chiron Technolas Keracor 116 Excimer Laser). However, central islands have been found to be essentially non-existent with excimer lasers having a Gaussian beam profile (such as the Summit ExciMed UV 200). A flat beam excimer laser has an energy profile with a generally "top-hat" shaped configuration with a marked distinction between the area within and outside the beam. The energy profile across the beam itself is relatively constant and homogeneous in a Gaussian beam profile the energy level of the beam increases toward its centre forming what is sometimes called a "hot" centre. In addition, the Gaussian lasers such as the Summit ExciMed LrV 200 produce essentially no central islands and do not utilize vacuum aspiration or nitrogen purging. The Summit ExciMed also has a pulse repetition rate of approximately twice that of the VISX Twenty Twenty flat beam laser, meaning that under the vortex plume theory the incidence of central islands should be greater as there is less time for plume dissipation.

The present invention therefore discounts the vortex plume theory. Instead a new basis to explain the formation of central islands has been developed. This new basis shall be referred to as the Acoustic Shock Wave model. Of underlying importance to the Acoustic Shock Wave model is the understanding that the excimer laser beam creates circular shock waves in the anterior stroma driving fluid both centrally and peripherally within the cornea. The intraoperative stromal hydration patterns are determined by the acoustic shock wave pattern, which is in turn related to the energy beam profile of the laser. Where there is progressive fluid accumulation there will be interference with oblation. That is, the stromal fluid accumulation blocks the successive pulses from the laser as the laser removes the fluid rather than the stromal tissue. The result of this process is the formation of central islands at the points where fluid accumulates and blocks oblation. Blowing nitrogen across the cornea reduces the formation of central islands by drying the central fluid pocket, thereby explaining the lower incidence of central islands for lasers which utilize nitrogen purging. However, nitrogen purging, through drying the stroma, results in additional problems including an increase in stromal haze, prolonged visual rehabilitation and an increase in irregular astigmatism. Furthermore, alcohol removal of the epithelium and the related alteration of stromal fluid dynamics has been found to reduce the formation of central islands as would be expected in light of this discovery.

It has also been found that larger optical zones impose a greater risk of inducing central islands owing both to the larger shock wave amplitude and the tendency of the laser beam energy profile to drop off in its centre as the diameter is increased. However, the use of larger optical zones is preferable as it is less prone to regression, results in better wound contours and reduced night glare. Once the optical zone exceeds approximately 3 millimeters, stromal fluid is driven both centrally and peripherally, much like the ripples formed after dropping a large ring into a pool of water. It is this central fluid accumulation that leads to the creation of central islands with homogeneous energy beam profile excimer lasers.

Bearing in mind this discovery, it has been found that treating or subjecting the central portion of the cornea to irradiation above and beyond that required for refractive correction, causes a dramatic improvement in qualitative visual results with the elimination of central islands for both myopic and astigmatic corrections. Such results have not previously been achieved. When combined with irradiation of the entire treatment area, the net effect is significant improvements in both quantative and qualitative visual results.

Typically when utilizing the method of the present invention, four types of eye drops are given to the patient beforehand. These drops can include an anesthetic to freeze the eye, an antibiotic to help prevent infection, an anti-inflammatory to reduce swelling and pain, and a pupil constrictor to reduce light sensitivity. After the various forms of medication have been given an opportunity to take effect, the patient's untreated eye is covered and the patient lies down on the patient bed for treatment. An alignment system is activated on the excimer laser to align the treated eye with the laser equipment. A target light is utilized and the patient is instructed to focus his attention on the target light in order to stabilize eye movement. To prevent blinking during treatment, an eyelid speculum is inserted into the patient's treated eye. At this point the laser is programmed for the patient's prescription.

The laser utilized in the procedure is an argon-fluoride gas ultraviolet laser having a wavelength of 193 nm. Other types of excimer lasers have been found to be unacceptable due to the characteristics of their radiation which can have mutagenic or cataractogenic effects. In addition, 193 nm ultraviolet radiation has been found to result in smooth ablation of tissue with negligible damage to surrounding tissue. There are a number of commercially available lasers that satisfy these requirements, including, the Chiron Technolas Keracor 116 Laser and the VISX Twenty/Twenty Excimer Laser System. These lasers have been found to be particularly effective due to their powerful laser head and homogeneous energy beam profiles which result in minimal hyperopic overcorrection, minimal regression, and minimal or no damage to adjacent non-irradiated tissue.

FIG. 1 shows a typical laser system pursuant to the present invention. The laser console 1 typically comprises a laser head 2, a bridge unit 3, and an operating microscope 4. Incorporated within the console is also a power supply 5 and a microprocessor control 6 which includes a monitor 7 and a pulse control 8. In operation the console is positioned next to a patient bed 9 such that the patient can lie upon the bed 9 with his or her eye positioned for treatment. Fixation means 10, used to assist in stabilizing patient eye movement, is attached to the laser console 1 over the patient bed 9. Normally fixation means 10 will comprise a non-irradiating targeting beam of light.

The laser head 2 contains a series of optical lens that focus and control the laser beam 11. Laser head 2 also contains means 12 to vary the beam diameter such that treatment of the central corneal tissue can be carried out independently of the irradiation of the entire treatment area. Normally means 12 would comprise a variable diaphragm which may be opened or closed to produce a beam of desired diameter. Where the diaphragm is closed to produce a small diameter beam, the blocked portion of the beam will be absorbed by the diaphragm. In an alternate embodiment, beam diameter may be controlled through internal laser optics.

Preferably the radiation is short pulsed and in the range of approximately 10 to 20 nanoseconds to minimize heat diffusion beyond the irradiated area. Pulses of this duration typically ablate a layer of tissue having a thickness of only a few molecules at a time to further reduce damage to adjacent tissue. Furthermore, the preferred fluence for the laser to operate at is 120 to 130 mj/cm2 which helps to promote optic longevity while reducing acoustic shock effects. It should be appreciated that both the pattern and the amplitude of acoustic shock waves play an important role in central island formation and that a fluence in the above range has been found to be optimal. Increasing laser fluence above these values has been shown to produce an undesirable thermal energy effect, increased degradation and increased acoustic shock wave effect. As has been determined by the present invention, it is the formation of such acoustic shock waves that can lead to the formation of central islands.

Once the patient is situated on the treatment bed with the laser calibrated and programmed, a circular optical zone marker is applied to the surgery area of the treated eye thereby defining a treatment area. The epithelium is then removed from the treatment area through the use of the laser, through wiping with a blunt optical instrument (such as a Paton spatula) or through the application of diluted alcohol drops. Following removal of the epithelium the patient is directed to focus on the targeting beam and the excimer laser treatment is commenced. A surgeon handpiece may be used to further immobilize the eye during the procedure.

Typically the first step involving the laser itself is the selective treatment of the central portion of the anterior surface of the cornea through subjecting the cornea in the treatment area to irradiation to ablate a portion of the tissue. This important first step is critical in the prevention of central island formation. It has been determined that when using the VISX Twenty Twenty Excimer Laser, for treatments of up to 6 diopters ablation of 1 micron per diopter is optimal. Ablation of about 0.6 microns per diopter has been found to be adequate for treatments above 6 diopters since large diameter treatments usually require deep ablations accomplished through multistep variable-diameter laser ablation. When using the Chiron Technolas Keracor 116 Laser, it has been determined that central corneal treatments of approximately 3 microns per diopter for treatment up to 3 diopters, 2.5 microns per diopter for treatments from 4 to 6 diopters, 2 microns per diopter for treatments from 7 to 9 diopters and 1.5 microns per diopter for treatments above 10 diopters are optimal. It has also been determined that treating an area of the cornea having a diameter of from 1 to 4 millimeters (with the preferable treatment zone being from 2 to 3 millimeters) in this manner is sufficient to prevent the formation of central islands. Following this treatment step, the entire treatment area of the cornea is subjected to irradiation causing volumetric removal of a predetermined depth of the corneal tissue through photoablative decomposition. That is, treatment of the central corneal tissue is in addition to full treatment of the entire treatment area and has no refractive effect. Rather, the procedure increases fie patient's qualitative vision and the ultimate optical performance of the patient's eye.

Through treating the central cornea/tissue as described, a central hollow or detent is created in the corneal tissue. It has been found that with a central treatment area having a relatively small diameter, the energy profile across the laser beam is sufficiently constant to prevent the formation of central islands through the effects of acoustic shock waves. That is, with small diameter central treatment zones stromal fluid is not driven in opposing directions to form central islands. However, acoustic shock waves produced during the irradiation of the full treatment area drive stromal fluid into the hollow or detent. The central treatment is thereby blended into the ablation with the full treatment leaving a generally smooth treated corneal surface. Patients are not overtreated during the process as the central treatment only removes tissue that should be removed and that would not have been removed if it were not for the central treatment step.

Figure 2:
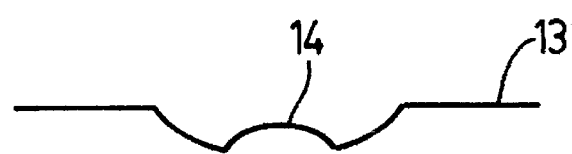
FIGS. 2, 3, and 4 are schematical drawings of the cornea of an eye showing the effects of various photorefractive keratectomical procedures.
Figure 3:
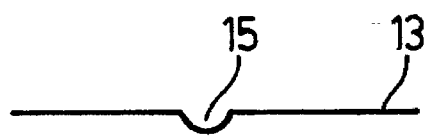
Figure 4:
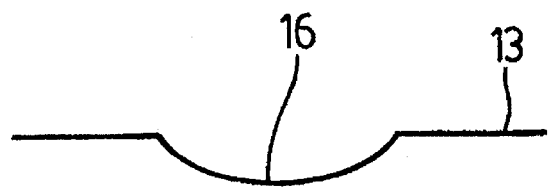

FIGS. 2, 3, and 4 show schematically in a simplified manner the net effect of the present invention as compared to the prior art. These Figures are meant to be simplified cross-sectional views of corneal tissue 13 that has been treated by photorefractive keratectomy. FIG. 2 depicts a central island 14 that often develops under current practices with current equipment. Compared to FIG. 2, FIG. 3 shows the corneal tissue after treatment of the central treatment area where irradiation of this such area occurs as a pretreatment step. In this instance a detent 15 is shown as having been created in the cornea. Finally, FIG. 4 shows the net result of ablation of the entire treatment area where the detent 15 has been blended into the ablation of surrounding tissue to form a relatively smooth surface 16.

In cases where patients would not normally have developed central islands, the relatively shallow central treatment detent has been found not to deleteriously effect the vision of the patient. It has been determined that the eye tolerates a facet or detent much better than a bump or central island. However, excessive central treatment (for the VISX Twenty Twenty excimer laser in excess of 2 microns per diopter) has been found to result in a refractive effect inducing hyperopia and may increase haze. Patients subjected to central treatment within the invention's parameters normally experience an improvement in qualitative vision due to an improvement in topography, even in those patients who would not have manifested a central island. In addition, with the current move toward larger optical treatment zones to reduce night glare and to improve wound contour to reduce haze and regression, central treatment pursuant to the present invention is even more important since the risk of central island formation increases with larger optical treatment zones.

Additional ablative treatment to the central cornea is also required for phototherapeutic keratectomy (PTK) procedures. In PTK, the optical zone is fixed and a large surface area is exposed in order to remove scar tissue, corneal irregularities or to remove the epithelium prior to PRK in a transepithelial approach. Due to the creation of acoustic shock waves and the formation of central islands, the same problems and concerns apply to PTK as to PRK and hence the need for the same type of central ablative treatment as discussed.

In an alternate embodiment of the invention, the epithelium in the treatment area is removed by the excimer laser at the same time that the cornea is ablated. In so doing the steps of removing the epithelium over the central treatment area and the central treatment step are combined into a single procedure, as are the removal of the epithelium over the rest of the treatment area and the irradiation of the entire treatment area.

It will also be appreciated that the central treatment step may be carried into effect at different stages of the procedure. In many cases the central treatment will be carried out as the initial step of the procedure representing in effect a pretreatment step. However, the treatment of the central corneal tissue in the described manner may also be carried out simultaneously with the ablation of the entire treatment area or it may be carried out as a subsequent step following ablation of the treatment area. When the central area treatment is performed prior or subsequent to the irradiation of the entire treatment area, the two steps of the procedure should be carried out sufficiently close together in time such that significant epithelium healing has not occurred.

It should be understood that what has been described are the preferred embodiments of the invention and that it is possible to make variations to these embodiments while staying within the broad scope of the invention. Some of these variations have been discussed while others will be readily apparent to those skilled in the art.

What is claimed is:

1. An improved method of ophthalmological surgery to change the optical characteristics of an eye through a primary treatment of the corneal tissue of the eye by subjection to ultraviolet irradiation to volumetrically remove a portion of said corneal tissue of said eye by way of photoablative decomposition, the method comprising the initial step of pre-treating a relatively small central portion of said corneal tissue with ultraviolet radiation causing photoablative decomposition of said central portion of said corneal tissue to a pre-determined depth, said pre-treatment of said central portion of said corneal tissue being over and above the primary treatment of said corneal tissue, said pre-treatment step increasing qualitative visual results of the ophthalmological surgery while not significantly changing the refractive characteristics of the corneal tissue.

2. The method as claimed in claim 1 further comprising the specific steps of:
   (i) removing a central portion of the eye's epithelial tissue thereby defining a treatment area;
   (ii) selectively pre-treating the eye's anterior corneal surface by subjecting said central portion of the corneal tissue in the treatment area to ultraviolet irradiation through the use of an excimer laser whereby a portion of the corneal tissue is volumetrically removed, to a pre-determined depth, through photoablative decomposition; and,
   (iii) thereafter fully treating the entire corneal tissue in the treatment area by subjecting said tissue to ultraviolet irradiation through exposure to an excimer laser causing volumetric removal of a portion of the corneal tissue to a predetermined depth by means of photoablative decomposition.

3. The method as claimed in claim 2 wherein the steps of subjecting the eye to irradiation comprise exposing the eye to an argon-fluoride excimer laser having a wavelength of approximately 193 nm whereby the irradiation causes minimal or no damage to adjacent non-irradiated tissue.

4. The method as claimed in claim 3 wherein said pre-treatment and said full treatment steps are carried out by irradiating said corneal tissue through exposure to a plurality of short pulses, of a duration from about 10 to 20 nanoseconds, of ultraviolet radiation from said excimer laser, each of said pulses ablating a layer of corneal tissue having a thickness of a few molecules.

5. The method as claimed in claim 4 wherein the step of selectively pre-treating the eye's anterior corneal surface by subjecting said central portion of the corneal tissue in the treatment area to ultraviolet irradiation comprises the step of irradiating an area of said corneal tissue of from 1 to 4 millimeters in diameter.

6. A method of photorefractive keratectomy for making myopic or astigmatic corrections to an eye and thereby improving the refractive characteristics of the eye, the method comprising the steps of:
   (i) selectively pre-treating the eye's anterior corneal surface by subjecting a small central portion of the eye's corneal tissue and the eye's epithelium to ultraviolet irradiation through the use of an excimer laser having a wavelength of 193 nm causing a portion of the eye's corneal tissue, together with the eye's overlying epithelium, to be volumetrically removed through photoablative decomposition; and,
   (ii) thereafter subjecting an enlarged area of the eye's corneal tissue to ultraviolet irradiation through exposure to said excimer laser causing volumetric removal of the eye's epithelium in the enlarged area and volumetric removal of a predetermined depth of the eye's corneal tissue in the enlarged area by means of photoablative decomposition.

7. A method for reducing the incidence of central island formation in an eye's cornea through minimizing the effects of acoustic shock waves within the eye's cornea during photorefractive keratectomy, the method comprising the steps of:
   (i) removing a central portion of the eye's epithelium thereby defining a corneal treatment area;
   (ii) forming a hollow or detent, having a diameter of approximately 1 to 4 millimeters, in a central portion of the treatment area through pre-treating the central portion of said eye's corneal tissue with an excimer laser having a wavelength of 193 nm; and
   (iii) thereafter fully treating said corneal treatment area through subjecting the treatment area to irradiation through exposure to said excimer laser causing removal of a predetermined depth of corneal tissue,
whereby acoustic shock waves created during the irradiation of the treatment area drive stromal fluid of the eye into the central hollow or detent.

8. The method as claimed in claim 7 wherein said step of removing a central portion of the eye's epithelium comprises removing the eye's epithelium through the use of said excimer laser, through wiping with a blunt optical instrument, or through the application of diluted alcohol drops.

9. The method as claimed in claim 7 wherein the step of fully treating said corneal treatment area includes utilizing said hollow or detent formed during said pre-treatment step to collect stromal fluid that is driven by acoustic shock waves created during said full treatment step such that following said full treatment step said corneal treatment area contains a relatively small, centrally located, hollow or detent having a depth of less than 2 microns.

10. A method for reducing the incidence of central island formation in an eye's corneal tissue through minimizing the effects of acoustic shock waves created within the eye's cornea during photorefractive keratectomy, the method comprising the steps of:
   (i) removing a central portion of the eye's epithelium thereby defining a corneal treatment area;
   (ii) forming a central hollow or detent, having a diameter of approximately 1 to 4 millimeters, in a central portion of the treatment area through pre-treating the eye's corneal tissue with an excimer laser having a wavelength of 193 nm; and,
   (iii) thereafter fully treating said corneal treatment area through subjecting the treatment area to irradiation through exposure to the excimer laser causing removal of a predetermined depth of corneal tissue, whereby acoustic shock waves created during the full treatment step drive stromal fluid of the eye into the central hollow or detent thereby filling and substantially eliminating the central hollow or detent.

* * * * *